United States Patent

Gust

(10) Patent No.: US 6,615,145 B2
(45) Date of Patent: Sep. 2, 2003

(54) DETERMINATION OF PARTICLE CHARACTER IN A VERTICALLY FLOWING FLUID

(76) Inventor: Giselher R. Gust, Zeppelinring 33 D-24146, Kiel (DE)

( * ) Notice: Subject to any disclaimer, the term of this patent is extended or adjusted under 35 U.S.C. 154(b) by 84 days.

(21) Appl. No.: 09/975,354

(22) Filed: Oct. 11, 2001

(65) Prior Publication Data

US 2002/0065615 A1 May 30, 2002

(30) Foreign Application Priority Data

Oct. 12, 2000 (DE) .......................... 100 51 715

(51) Int. Cl.[7] .............................................. G01F 7/00
(52) U.S. Cl. ........................... 702/45; 702/26; 702/50; 702/100
(58) Field of Search .................... 702/33, 45, 49, 702/50, 23, 24, 26, 100; 210/85, 155, 156, 162, 163, 166; 73/152.23, 152.51

(56) References Cited

U.S. PATENT DOCUMENTS

| | | | | |
|---|---|---|---|---|
| 3,666,101 A | * | 5/1972 | Rosaen | 210/90 |
| 4,762,009 A | * | 8/1988 | Scrudto | 73/863.52 |
| 5,614,236 A | * | 3/1997 | Klang | 426/112 |

OTHER PUBLICATIONS

Giselher Gust, et al, "Particle accumulation in a cylindrical sediment trap under laminar and turbulent steady flow: An experiment approach," Aquatic Sciences, Birkhauser Verlag (Basel, Germany), vol. 58 (No. 4), p. 297–326, (Oct. 3, 1996).

G. Gust, et al, "Mooring line motions and sediment trap hydromechanics: in situ, intercomparison of three commom deployment designs," Deep–Sea Research I, Elsevier Science Ltd. (Germany), vol. 41 (No. 5/6), p. 831–857, (1994).

Hans–Peter Kozerski, "Possibilities and limitations of sediment traps to measure sedimentation and resuspension," Hydrobiologia, Kluwer Academic Publishers (Belgium), p. 93–100, (1994).

\* cited by examiner

*Primary Examiner*—Bryan Bui
(74) *Attorney, Agent, or Firm*—Larson & Larson, PA; James E. Larson

(57) ABSTRACT

An apparatus and method for determining particle character moving with a vertical fluid flow towards a multiplet of calibrated sediment traps. The number N of measuring locations, which coincides with the number of n different particle groups ($P_n$) occurring at all of them, with N (N=n) different types of sediment traps ($T_N$) the mass accumulations ($M_{TN}$) and the sinking/raising velocity spectrum (VW) of the n particle groups are determined. Upon formulation and solution of a linearly independent system of [N] accumulation equations under incorporation of the established calibration and measurement parameters, the sought-after in-situ mass flux [$(ISM)_{Pn}$] and the derived in-situ total mess flux [$(ISM)_P$] is obtained.

23 Claims, 2 Drawing Sheets

DETERMINATION OF PARTICLE CHARACTER IN A VERTICALLY FLOWING FLUID

PRIOR APPLICATIONS

This application bases priority on German application no. 100 51 715.3-52 filed on Oct. 12, 2000.

BACKGROUND OF THE INVENTION

1. Field of the Invention

The invention relates to a procedure for the systematic determination of substances with particle character, moving with a vertical component in a flowing fluid, for the mass accumulation of particle groups in a calibrated sediment trap exposed to flow with knowledge of the actual values of the trap and flow parameters, and to an apparatus for executing this procedure.

2. Description of Prior Art

Materials with particle character, moving with a vertical component in flowing waters and oceans, play an essential role in sedimentological, biogeochemical, biological, climate-relevant, morphological and many other processes. Their systematic determination leads, among others, to detailed results regarding the global cycle of organic carbon and nutrients. Likewise, many technical installations with moving fluids require information about the vertical mass flux of embedded substances with particle character. In connection with the present text, the term "materials with particle character" is to be understood as representing both particles consisting of solids (either fully solid or aggregated) in the sense of "particles" as well as particles consisting of gas bubbles or solid-gas combinations. Depending on relative density of the particle type it experiences, either a sinking force (sinking materials) or a buoyancy force (raising materials). In the state-of-the-art, the major group considered in connection with sediment traps is that of sinking particles, which is the reason why the following text mostly refers to this type. The devices used according to the state-of-the-art for determination of the vertical mass flux (so called "sediment traps") collect—even at the same measuring location—individually different amounts of sinking particles due to the different collection and extraction procedures and apparatus used. For these cases the prominent task was to determine qualitatively and quantitatively the composition of the pool of a sinking substance with particle character rather than to determine the "in-situ mass flux" of the different sinking particle groups it is comprised of in the sense of knowledge of the exact values of actually sinking mass and the detailed sinking processes in the fluid. The equation used accordingly by which the so called "trap flux" is determined by dividing the particle mass collected in the sediment trap by collection time and total area of the trap aperture (the opening area of a sediment trap), only permits one to calculate the mass flux of sinking particles and related variables in the open water column for fluids without motion.

In case the fluid carrying particles moves with a horizontal flow component towards the trap aperture which is typically horizontally aligned, then the actual collection process in the trap is strongly altered by the approach velocity in comparison with the sinking or sedimentation process in the free water column or at the bottom, respectively. A circulation pattern of the fluid is generated which is coupled to the approaching flow in the entrance zone of the trap, which thus is continuously flushed by new fluid. This "circulation zone" permits particles embedded in the fluid to reach not only gravimetrically but also advectively the inner space of the trap from where a fraction settles. This holds for particles with a sinking speed larger than 5 m/day, slower-sinking particles, whose fraction of the total mass flux is mostly less than 10%, can only be collected by other techniques. The flow-influenced collection process of sinking substances with particle character cannot be quantified by the classical trap flux equation for non-moving fluid (mentioned above) and is reflected mathematically in semi-empirical "accumulation equations", by the help of which from the measured mass accumulation of a known, calibrated type of trap the in-situ mass flux of a single particle group can be calculated.

Here, the term "type of trap" is to be understood as a trap parameter specification based on coefficients related to an individual trap as sub-group of a "trap family" as the higher classification level. Such accumulation equations exist for different trap families, in particular for cylindrical and conical traps (see Reference 1 of Gust et al: "Mooring Line Motions and Sediment Trap Hydromechanics: In-Situ Intercomparison of Three Common Deployment Designs" 1994, Deep Sea Research 41, 831–857 and Reference 2 of G. Gust et al.: "Particle Accumulation in a Cylindrical Trap under Laminar and Turbulent Steady Flow: An Experimental Approach" 1996, Aquatic Sciences 58, 297–326) and plate traps (see Reference 3 by B. Westrich 'Fluvialer Feststofftransport-Auswirkungen auf die Morphologie und Bedeutung fuer die Wasserguete' 1988, Schriftenreihe Wasser-Abwasser 22, R. Oldenbourg Verlag, Muenchen, Wien, pages 24–29). The development of additional accumulation equations for other trap families is presently a research task. These can be incorporated without problem into the invention described here since they will be based on the same basic concepts. Particularly, Reference 2 provides basic explanations for the mass accumulation of particle groups in a calibrated sediment trap under flow as basis for the invention presented here. An excerpt for the necessary understanding of the invention is offered in the following. The accumulation equations presented in References 1 and 2 show that sediment traps of cylindrical and conical geometry operate on a basically different particle-collection principle compared to plate traps with flat, hydraulically smooth or rough surfaces. For example, for plate traps (see patent DE 197 37 448 A1) the particles settle immediately from the moving fluid onto the trap surface as soon as the deposition stress is larger than the counteracting flow-induced bottom stress at the collection location. In case the flow-generated bottom stress exceeds this value, the particles cannot settle any more. If the bottom stress reaches with increasing flow speed the critical bottom stress, then the particles which had already settled on the collection surface are eroded again. The plate traps thus provide a mean value of mass for experiment duration and collection area, which depends on the deposition stress of the sinking particles, on the flow-generated bottom stress, on the critical bottom stress for erosion of deposited particles as well as on the respective initial concentration of particle groups with different settling velocities. In contrast, for sediment traps with hollow geometry the accumulation process under flow leads via a trap-internal circulation pattern which is coupled to the outer flow and whose fluid flushing rate depends on the velocity of the approaching fluid. From the deepest section of this circulation zone where the particles are carried along with the fluid while sinking, a fraction of particles as described by the so called "yields function" is transferred into the underlying quiescent fluid zone where the particles are moving downwards exclusively by their sinking velocity and eventually settle on the collection surface. This type of collection process leads via the experiment duration to the cumulative increase of mass collected (mass accumulation). The quiescent zone beneath the circulation zone is required in both design and function and exists only for a proper length-width ratio of the trap geometry.

For a single, vertically aligned sediment trap the following accumulation equation holds for a substance comprised of a mixture of sinking particles (Gust et al., 1996)

$$M_{TP} = \Sigma(M_T)_n = \Sigma y(u_a, w_{sn}) c_{0n} t(Q(u_a) + A_s w_{sn}) \quad [1]$$

For a single conical trap, a dependency of simular mathematical structure but with additional controlling parameters is assumed:

$$M_{TP} = \Sigma(M_T)_n = \Sigma(y(u_a, w_{sn}, TKE) c_{0n} t(Q(u_a) + A_s W_{sn})) \quad [2]$$

For a single plate trap the following accumulation equation can be cited according to Westrich (1988):

$$M_{TP} = \Sigma(M_T)_n = \Sigma(c_{0n} w_{sn}(1 - \tau/\tau_d)) \quad [3]$$

The terms used in equations [1],[2] and [3] mean:
active trap aperture $A_s$: that section of the total trap aperture A through which the particles are transported into the interior of the trap;
approach velocity $u_a$: velocity of the approaching fluid flow in which the particles are embedded;
fluid flushing rate $Q(u_a)$: the amount of fluid transported per unit time through the trap interior, measured at the trap aperture (depends on the approach velocity and on the trap geometry);
mass accumulation $M_{TP}$: total particle mass which remains in the trap during the selected time interval t under given flow, particle and environmental conditions; the particle group mass accumulation $(M_T)_n$ identifies the mass of the particle group n which shows mean sinking or raising speed $w_{sn}$ (either as single particle or as mean value of a particle group with the running index n); the sum of all sinking/raising velocities forms the sinking/raising particle velocity spectrum with information on how the total mass accumulation $M_{TP}$ is distributed over the n particle groups ("particle spectrum");
particle concentration $c_{0n}$: initially present mass per fluid unit volume (identified by number, volume, and density of the particles) for a particle group n;
TKE: turbulent kinetic energy, here particularly referring to the region immediately above the collection cup of conical traps;
yield function $y(u_a, w_s)$ experimentally determined function describing the fraction of a particle group n which is moving with the circulation cell (describes the dynamic transport process in the circulation zone) through the trap and is retained;
$\tau$: bottom stress $\tau$ in a trap
$\tau_d$: deposition stress in the trap A relevant parameter to be derived via the mass accumulation of the systematically quantified substance with particle character in a moving fluid is the particle group in-situ mass flux $(c_o w_s)_n$ of those n particle groups which are retained in a trap and which add up to a total in-situ mass flux $\Sigma(c_o w_s)_n$. Its determination by equation [1] with a single trap is only possible when particles of a single particle group with a single settling/raising velocity $w_{s1}$ are exclusively collected. In nature, generally more than one particle group exist simultaneously, which are classified by the particle sinking/raising velocity spectrum. In case this exists, determination of the in-situ mass flux from n separate particle groups and of the in-situ total mass flux of the particle spectrum under flow by use of a single trap type is not possible. Use of such single-trap designs is presently the basis of all known devices to collect sinking particles.

Regarding the known devices for the execution of current collection and extraction procedures with existing patents, sediment traps are described which are not able to determine the in-situ vertical mass flux under flow. For example, in patent DE 29514173U1 and U.S. Pat. No. 4,869,118 an apparatus is described which is only identified for use in quiescent water. In other devices, no internal no-flow zones exist for the purely gravitational settling of particles beneath the trap-internal circulation zone. Stirred or pumped samples are investigated, instead (DE 3430263A1). Other proposed devices cannot be deployed on oceanic environments at depths in-situ (DE 9211263U1) or have insufficient geometries to prevent the resuspension of settled particles on the bottom when the approach velocity increases (DE 29520919 U1). Additionally, devices exist for the control of exclusively gravitationally operating sedimentation systems with stirrer (WO96/33000A1). The patent DE 19737448A1 describes a plate trap, for which the sedimentation equation is known and by which near the bottom a relatively unbiased collection rate of depositing material can be obtained as long as no erosion events occur during the collection time. This trap operates by another collection principle than traps with hollow geometry. Furthermore, other known patents (U.S. Pat. Nos. 4,762,009; 3,715,913) use a single trap for mass collection, in some cases also in multiples for replication of the results (DE 29520919U1). Concepts with purposefully selected different trap types are not in use.

The known state-of-the-art in collecting particles in a fluid body can be summarized such that in sediment traps with both hollow and flat geometries the mass accumulation occurs according to physical laws which are individually determined by the combination of trap type and family, flow as well as particle characteristics at the collection site. The consequently arising variation of the different controlling variables and resulting mass accumulations stretch under real-world conditions over a wide margin. To date, the use of single traps under flow—even at such low velocities as 1 cm/s—can not generate the in-situ mass flux of n particle groups comprising the substance to be determined from the mass accumulation. Even use of several traps of the same family and even type for statistical confirmation of the collection result does not lead to a conclusion about this parameter.

SUMMARY OF THE INVENTION

It is thus the task of the present invention to provide a suitable procedure to systematically determine substances of particle character in moving fluids by which the vertical particle flux and from it derivable additional particle parameters as relevant in-situ parameters can be obtained from those particle groups of the substance to be determined in the open-water column which contribute to the mass accumulation in a sediment trap. Furthermore, an apparatus is to be presented which, based on a calibrated type of sediment trap and a current meter, which is particularly suited to execute such procedure yet remains simple in design and handling. Altogether the measuring sites are not to be restricted to oceanic environments but extend to all limnic, fluvial and technical regions as well.

It is only from a thorough understanding of trap-specific mass accumulation equations of particles (or potentially also other particle-specific characteristics) that the procedure described in the invention for determination of the vertical in-situ mass flux of individual particle groups from the total mass accumulation under flow in a calibrated sediment trap can be developed. The invented procedure thus consequently represents a straight forward development of the insights which have emerged over the past years regarding the relevant in-situ parameters of substances with particle character under flow. While to date a differentiation between these relevant parameters was not possible and the in-situ determination limited to substances comprised of merely a single particle group, now all particle-type substances with an arbitrary number n of different particle groups can be identified usefully and categorically in their in-situ parameters. Relevant for the procedure is, that a number N of measuring locations is selected within the measuring region which agrees with the number n of individual particle groups which comprise the particle spectrum and where in each case the total particle spectrum contributes—though in different mass fractions for different trap types—to the mass accumulation. Together with the sinking/raising velocity spectrum of the n different particle groups a system of equations is available via the above-cited accumulation equations with a total of N equations which can be solved for the respective values of the concentration of the n particle groups as unknown variables under knowledge of the additional calibration and measurement parameters. From this follows under combination with the associated sinking/raising speeds by calculation the respective value of the vertical in-situ mass flux of the n different particle groups as well as desired characteristic bulk parameter the total in-situ mass flux prevailing at the measurement site (for very slow-sinking particles other procedures are to be used) of the particle spectrum of the substance with particle character investigated.

An essential requirement for obtaining a solution for a system of N equations is the linear independence. An equation is not allowed to be transformable into another one merely by multiplication by a constant. This is achieved in the invented procedure by providing at the N measuring locations, the sediment traps located there are independent trap types which a clear distinction in their trap parameters, in particular their geometric dimension. Thru the geometric design, different sediment traps—even under geometric similarity—show individual collection behavior which furthermore depends on the existing flow and particle parameters. Demonstration of geometric similarity between individual trap types has not been reported to date. Such traps would not be suited for use at the measuring locations. The selection of the trap parameters has to include adequate discrimination between the parameters such that the unavoidable measurement errors of the different parameters do not have an influence towards a linear dependence. Only a selection of individual parameters beyond this range of measuring uncertainly, which is to be established via solutions of the conditioning problem for the procedure and the apparatus, guarantees the required linear independence of the individual equations within the system of equations. All parameters used in the N equations of the linearly independent equation system have indices in accordance with the existing number n of different particle groups comprising the substance with particle character to be determined. For each of the N equations thus follows a corresponding specific set of values of the parameters involved. A variable with index is also the collection time interval, within which the different mass accumulations build up in the traps. For the collection time interval any reasonable value can be selected. For the general case it follows that the N individual traps can be operated at different times and for different duration in a regional measuring area under the condition that the other parameters are known in their time history of value assignment as well and all n different particle groups are always collected. According to a favorable realization of the invented procedure, it is provided that the start of the selected collection time intervals for each of the N particle traps is identical and all collection time intervals have the same length. In this synchronized case, it is warranted that the environmental parameters coincide for all traps. In addition, a simplification is given in the calculation of the variables when all collection times are identical.

Each of the n particle groups has a characteristic vertical velocity component (particle sinking or raising velocity) in the fluid column, also when exposed to current flow, which establishes the sinking/raising velocity spectrum. The determination of the sinking/raising velocity spectrum of the n particle groups can be established in different ways. In addition to special protocols, for example by an independent sinking velocity apparatus (settling chamber method—SCM, see Reference 4 of H.-P. Kozerski 1994 "Possibilities and Limitations of Sediment Traps to Measure Sedimentation and Resuspension", Hydrobiologica 284, pp. 93–100), methods to determine the sinking/raising velocity spectrum can be chosen such as mathematical optimization techniques or procedures with access to known data sets, for example from literature sources and data banks. Particularly simple and thus advantageous is the approach, as shown in a reduction to practice of the invention, to measure the sinking/raising velocity spectrum of the n particle groups optically, particularly at a location without moving fluid. Optical procedures are simple and permit a high measuring accuracy for reproducible measurement results. The sinking/raising velocity spectrum can optically be determined at many locations within the regional measuring area to validate the single measuring values. Exist are quiescent fluid zones at the measurement location without fluid being flushed through, yet nevertheless registration of all measurable particle groups n is ensured, then in such tranquil zone optical measurements are particularly advantageous. It suffices to chose hereby only one single optical measuring site, since determination of statistical mean values is not necessary.

Already in the introduction of the description, the issue was addressed that concerning the term "particle character" of substances with particle character both sinking as well as raising substances are meant, as result of which alternatively sinking and raising velocities are introduced as well. According to another favorable realization of the invention it is thus possible, that the n different particle groups comprising the systematically to be determined substance with particle character are formed by solid particles with sinking behavior or by combinations of solid and gaseous substances of different mixing ratios with raising behavior in the moving fluid. The describing parameters are identical for sinking and raising substances, a difference is only given in the sign of the sinking and raising velocity, respectively. Thus, no different conditions arise for the invented procedure from its application for either solid or gaseous particles, it has only to be ensured that the particle types moving in directions with different vertical components are properly collected according to the applicable accumulation equations. Consequently, as a rule, either only raising or only sinking particles can be determined.

An essential element for executing the procedure is the sediment trap (or gas trap). This can belong to different families (cylinder, cone, or boundary layer resp. plate trap) and be designed differently regarding its geometric dimensions in each case. Each realization of a sediment trap thus represents an individual trap type. From the invented procedure follows immediately for the execution of the procedure an arrangement of a minimum of N individual sediment traps which are placed at least at N measuring locations within a regional measuring region with moving fluid, all of which collecting the n different, measurable particle groups. Here self-contained sediment traps can be used of the same or also of different trap family in geometric variations which are optimized for the different measuring tasks at hand and may, for example, serve also other measuring tasks or are primarily deployed in the region for this purpose. Using more traps than necessary for the collection of n particle groups merely leads to an over-defined system of equations. Then individual, most suitable traps can be selected, or the values from the excess trap can be used for error statistics, for example. In case of an under-determined equation system, the number of traps is to be augmented accordingly. Upon knowledge of the trap and flow parameters, by the invented procedure an in-situ link between these N autonomous sediment traps and the n different particle groups of the substance to be determined can be established. To proceed, the mass accumulations in the N sediment traps and the sinking velocity spectrum (or raising velocity spectrum for raising particles) of the n particle groups has to be determined. For such setting, each trap has to be fully instrumented and be handled independently.

In addition to this general type of apparatus for executing the protocol it is, however, starting from at least one calibrated sediment trap of one trap family assigned to a collection cup and a flow sensor, particularly advantageous when an invented apparatus is selected which, for the determination of the vertical in-situ flux of n different particle groups and the in-situ total mass flux of the particle spectrum, which can be derived from this, of the substance to be determined in a free water column of a regional measuring site, consists of a trap multiplett with a number N of particle traps congruent with the n particle groups with type-specific trap parameters and assigned collection cups which are oriented against the direction of the sinking/raising movement of the n particle groups. With the term "multiplett" the combination of neighboring traps is expressed, all of which are used to measure the same physical quantities. Such a multiplett represents a complete measuring unit and is simple to deploy and easy to handle. Due to the close neighborhood of the individual traps, a correct positioning within a regional measuring site is ensured, such that in any case all traps collect from the same existing particle spectrum the accumulated mass. Furthermore, an individual instrumentation is not necessary. With commonly used single instruments the respective parameters can be determined for the whole multiplett. The orientation of the collection cup against the sinking or raising movement of the particles ensures that both types (either sinking or raising substances) can be collected. The respective particles to be collected move into the collection space and remain there.

Depending on the type of the existing n particle groups and the moving fluid different trap families, identified either as particle or gas traps, are particularly suited for the collection process. Thus it is a favorable realization of the apparatus to execute the invented procedure to select the N particle traps with type-specific trap parameters from different trap families. The variation by individual trap types within one trap family is necessary in order to ensure the linear independence of the coefficients of the equation system. As shown above, different trap families obey different accumulation equations, which accordingly are incorporated into a system of equations leading in same manner to a solution for the sought-after particle parameters. Additional trap and flow parameters, for example the bottom stress and the deposition stress of plate traps, are then to be determined by calibration of these traps in the laboratory or in the field, and by measurement of the flow velocity during the field investigation. On the basis of the respective trap, flow and particle parameters each trap type collects different mass accumulations according to the accompanying accumulation equation, for traps with hollow geometries (cylinder and cone traps) according to equations [1] and [2], respectively. Due to the especially advanced insights into the behavior of these trap families, which are condensed in the experimentally confirmed semi-empirical accumulation equations, it is thus according to a realization to practice particularly advantageous when at least one of the N particle traps is shaped as trap with hollow geometry, and in particular as cylinder trap with a quiescent settling zone above the collection cup. The quiescent zone, which in a hollow cylinder lies beneath both the circulation cell which can be comprised of several eddies at its deepest section for higher approach velocities and the subsequent transition zone, is a relevant space in the cylinder trap since the fluid here is free of velocity effects.

The sinking/raising velocity spectrum can be determined at varied locations in the fluid by different procedures and devices. Outside a trap it has to be considered, though, that non-trappable particle groups due to their low vertical velocity need to be compensated for. A location, at which only those particle groups are found which are also collected by a trap is the quiescent zone inside cylinder traps. A plate trap can be considered as a quiescent zone over its complete upward-facing surface. In a quiescent zone the caught particles are exposed to very little or no flow-related influences. In a further advantageous realization of the invention it is thus particularly useful when for at least one sediment trap, in particular in the quiescent zone of a particle trap with hollow geometry, an optical sensor to register the sinking/raising velocity spectrum of the n particle groups is incorporated. As optical sensor an optical recording unit (a video camera) may be selected. In this way, by simple means highly accurate, reproducible measuring results of the sinking/raising velocity spectrum can be obtained. A compensation based on measuring or mathematical techniques for non-trappable particle groups is thus not necessary.

A particular problem in the use of sediment traps is the removal of the mass accumulated from the assigned collection cups, which is also valid for the trap multiplett. In order to avoid on one hand continuous emptying which would always require a recovery of the sediment trap deployed and, on the other hand, to avoid also too large collection cups with long exposure times during which changes in the collected particle groups are unavoidable, it is of advantage according to another realization of the invention to equip the trap multiplett with a movable, particularly rotary sample magazine equipped with a multitude of sampling cups which can be assigned freely to the individual sediment traps. Such sample magazines are state-of-the-art in connection with a variety of collection devices and can be realized in a multitude of versions. Important is the unambiguous connection between the different collection cups and sets of measurement results. For the trap multiplett, linearly moving magazines with single or multiple row design can be used with appropriate parallel motion of the collection cups. For sediment trap types held in fixed positions, circular magazines can be used as well where the collection cups are mounted in a circle-shaped guide permitting slip motion on a circular path. Of advantage is in this case particularly the stable and compact arrangement of the collection cups which consequently permits a favorable spatial arrangement of the sediment traps. In the sense of unambiguous links of values collected it is furthermore useful in another favorable realization of the invention that the collection cups are opened and closed via an individual timing program which is particularly based on the occurrence of events. Such events could be reaching a particular filling level of the collection cup as well as certain environmental events such as particle clouds.

In connection with a sampling magazine and a timed control of the collection cup connections with the trap multiplett, the invented procedures for determination of substances of particle character can be automated in a particularly simple way. For example, in connection with particular environmental hazards or other harmful substances in the fluid or with particular flow events in the fluid it may additionally be useful to position the trap multiplett at different heights in the moving fluid. This can, for example, be achieved by a mooring line by which the trap multiplett can also be simply deployed and recovered. Further explanations of type and sequence of executing the procedure are to be taken from the particular description section.

Beforehand, it should be noted that the explanations presented here are based on the particle-relevant parameters, particle concentration and sinking/raising velocities. The concentration is a characteristic parameter which will always arises in connection with information about individual particle groups of the total particle spectrum. In lieu of the sinking or raising velocities the particle groups could also be classified by the behavior of so called "tracer characteristics" which may be coupled to the single particles of the respective particle groups. The presentation of associated tracer fluxes would then be provided by tracer accumulation equations.

BRIEF DESCRIPTION OF THE FIGURES

The character of the invention regarding procedure and apparatus for execution of the procedure is subsequently explained in detail based on the schematic figures wherein.

DETAILED DESCRIPTION OF THE INVENTION

Figure 1:
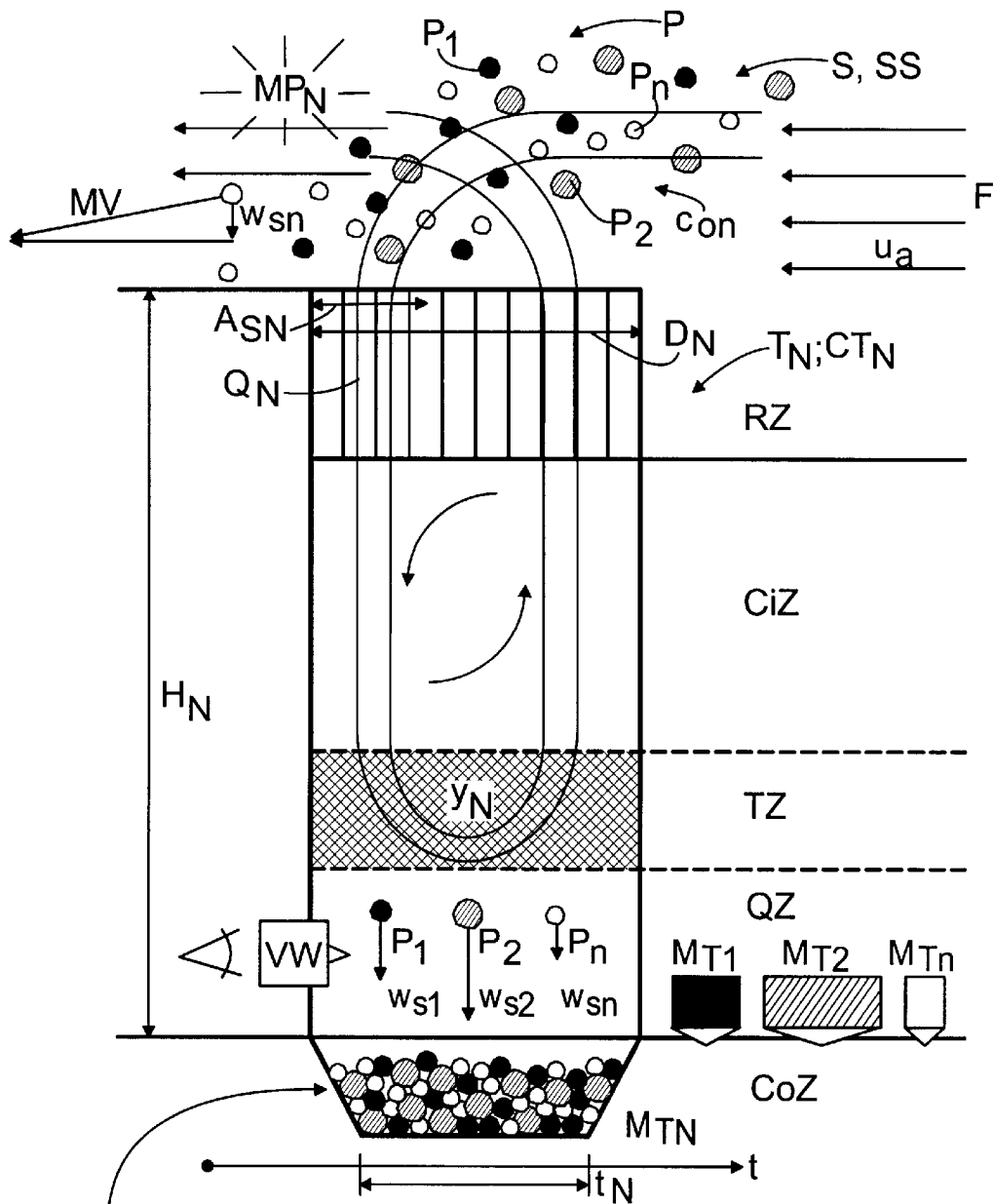
FIG. 1 for the invented procedure is a simplified presentation of the situation of a parameterized cylinder trap.

FIG. 1 shows a calibrated cylinder trap $CT_N$ as representative of a general trap T (family and type) with a ratio of height H to diameter D of roughly 8 to 1 in a regional measuring site MA with fluid F moving with an approach velocity $u_a$. The running index N shows the position of the trap within the multiplett (compare with FIG. 2) and consequently the measuring location $MP_N$. A substance S with particle character consists of particle groups $P_1, P_2, \ldots, P_n$ carried along by the fluid at respective concentrations $c_{on}$, with n representing the running index for all measurable particle groups $P_n$ comprising the trapped particle spectrum P. In the demonstration example selected a sinking substance SS with sinking particle groups $P_1, \ldots, P_n$ is chosen. These show a movement vector MV, of which the vertical component establishes the sinking velocity $w_{sn}$. In case of raising gas bubbles as particle groups latter vector would have the opposite orientation. The sinking particle groups $P_n$ reach through the active trap aperture $A_s$ together with the fluid flushing rate $Q_N$ at first the baffle zone RZ as part of a circulation zone CiZ of the cylinder trap $CT_N$. Those fractions of the particle groups $P_n$ which are not carried through the circulation zone CiZ into the quiescent zone QZ are expelled by the circulation cell, which as dynamic transport process in the circulation zone CiZ provides the coupling of the trap interior to the flow outside the trap in the fluid F. Via the empirically determined yield function $y_N$ of the cylinder trap it is determined which fraction of the particle groups $P_n$, after the transition zone TZ, reaches the quiescent zone QZ. Only particle groups $P_1, \ldots, P_N$ having reached the quiescent zone QZ and whose sinking velocity spectrum VW can be determined here in a simple and accurate manner, are collected in the sampling zone CoZ at the bottom of the cylinder trap $CT_N$ and form the trap-associated mass accumulation per unit time (also "collected mass") of which the origin lies in the concentration $c_{on}$ of the particle groups $P_n$ in fluid F.

In the following, a system of equations [N=I, II, III] is exemplary presented for a multiplett TM for a number n=3 of sinking particle groups $P_n$ contributing to the accumulation process. By establishing a system of equations with N=3 equations ($M_{TI}$, $M_{TII}$, $M_{TIII}$) which, based on the proper selection of the geometry of N=3 trap types $CT_N$, are linearly independent, and from which upon inserting the obtained measuring, collection and calculation data, the in-situ concentrations $c_{o1}$, $c_{o2}$, $c_{o3}$ of the three particle groups $P_1$, $P_2$, $P_3$ can be determined and from these in turn, under inclusion of the associated sinking velocities $w_{s1}$, $w_{s2}$, $w_{s3}$, the respective vertical in-situ mass flux $(ISM)_{P1}$, $(ISM)_{P2}$, $(ISM)_{P3}$ of the individual particle groups $P_1$, $P_2$, $P_3$ and from these the resulting in-situ total mass flux $(ISM)_P$ for the particle spectrum P as relevant particle parameters.

When during the collection time intervals $t_N$ the approach velocity $u_a$ changes due to the environmental conditions and thus the flow-dependent trap variables $Q_N$ and $y_N$, then approximation techniques or numerical solutions for a corresponding number of equations have to be selected. Equation [IV] describes the accumulation behavior of a plate trap. As additional parameters wall shear stresses t arise here. This equation [IV] can also be used as additional equation when n=4 different particle groups $P_n$ exist. In general, based on the number n of particle groups Pn present, mixed equation systems of the respective accumulation equations for chosen combinations of varied calibrated trap types of different trap families are possible.

$$M_{TI} = c_{o1}(y_{I1}t_I(Q_I + A_I w_{s1})) + \qquad [I]$$
$$c_{o2}(y_{I2}t_I(Q_I + A_I w_{s2})) + c_{o3}(y_{I3}t_I(Q_I + A_I w_{s3}))$$

$$M_{TII} = c_{o1}(y_{II1}t_{II}(Q_{II} + A_{II} w_{s1})) + \qquad [II]$$
$$c_{o2}(y_{II2}t_{II}(Q_{II} + A_{II} w_{s2})) + c_{o3}(y_{II3}t_{II}(Q_{II} + A_{II} w_{s3}))$$

$$M_{TIII} = c_{o1}(y_{III1}t_{III}(Q_{III} + A_{III} w_{s1})) + \qquad [III]$$
$$c_{o2}(y_{III2}t_{III}(Q_{III} + A_{III} w_{s2})) + c_{o3}(y_{III3}t_{III}(Q_{III} + A_{III} w_{s3}))$$

$$M_{TIV} = c_{o1}(w_{s1} - w_{s1}(\tau_{IV}/\tau_{d1})) + \qquad [IV]$$
$$c_{o2}(w_{s2} - w_{s2}(\tau_{IV}/\tau_{d2})) + c_{o3}(w_{s3} - w_{s3}(\tau_{IV}/\tau_{d3}))$$

Figure 2:
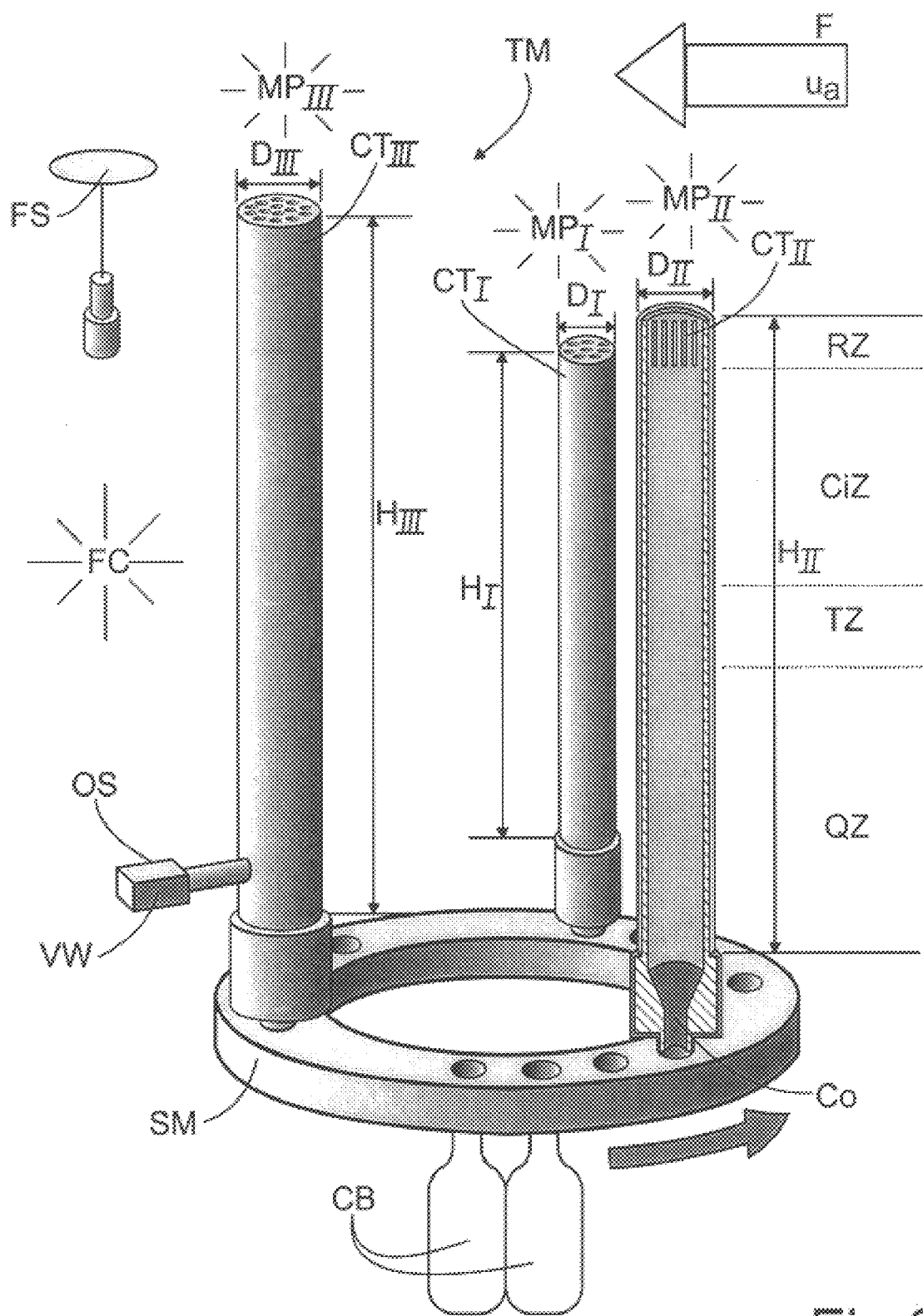
FIG. 2 is a trap multiplett as advantageous realization to practice of the apparatus to execute the procedure.

In FIG. 2, an apparatus is shown in perspective to execute this generally valid protocol. It consists of a trap multiplett TM with three independent, synchronously operating cylinder traps $CT_I$, $CT_{II}$, $CT_{III}$ with a length-diameter-ratio ("aspect ratio") H/D of 8:1 (minimum) and of inner diameters of $D_I$=45 mm, $D_{II}$=70 mm and $D_{III}$=100 mm, respectively. The dependence of the trap parameters $Q_N$ ($u_a$) and $y_N$($u_a$, $w_s$) from the approach velocity $u_a$ and the particle sinking velocities $w_{sn}$ are determined through trap calibration experiments. The active trap aperture $A_s$ is different for each of the trap types $CT_I$, $CT_{II}$, $CT_{III}$, respectively, yet nearly constant under changes in approach velocity. For the selected geometries a linear independence of the accumulation equations [I, II, III] is warranted.

For higher approach velocities $u_a$ a quiescent zone QZ still exists beneath the circulation zone CiZ inside the traps $CT_I$, $CT_{II}$, $CT_{III}$. In the reduction to practice, used as example, the sinking velocity spectrum VW is recorded by an optical sensor OS (video camera) exclusively in the quiescent zone QZ of cylinder trap $CT_{III}$. The flow F in the open water column FC is measured by a flow sensor FS. The solution of the equation system [N=I, II, III] for a synchronous time interval $t_I = t_{II} = t_{III}$ for mass collection leads under knowledge of all trap and environmental parameters in unison with that of the sinking velocities $w_{sn}$ to the concentrations $c_{on}$ of the three fastest-sinking collected particle groups $P_1$, $P_2$, $P_3$. In the existing validation case these groups are determined by mean sinking velocities of $w_{s1}$=5 m/d, $w_{s2}$=15 m/d, and $w_{s3}$=30 m/d. From the product of the calculated concentrations $c_{on}$ and the measured sinking velocities $w_{sn}$ follow the group-specific in-situ mass flux values $(ISM)_{Pn} = (c_o w_s)_n$ and the trap-derived in-situ total mass flux $(ISM)_P = (c_o w_s)_n$.

The three cylinder traps $C_{TI}$, $C_{TII}$, $C_{TIII}$ of the trap multiplett TM are mounted in locally fixed positions above a rotary sampling cup magazine SM which carries a sequence of individual collection cups CB. These are connectable via cones Co with the single cylinder traps $C_{TI}$, $C_{TII}$, $C_{TIII}$ and are rotated in time intervals $\Delta t$ by electronic circuitry not shown in the figure such that for chosen time intervals $t_N$ sampling is done synchronously.

List of Abbreviations

| | |
|---|---|
| $A_s$ | active trap aperture |
| $c_{On}$ | concentration of particle group $P_n$ |
| CB | collection cup |
| CiZ | circulation zone |
| CoZ | collection zone |
| $CT_N$ | calibrated cylinder trap N |
| $D_N$ | diameter of trap N |
| F | moving fluid |
| FC | free fluid or water column |
| FS | velocity sensor |
| $H_N$ | height of trap N |
| $(ISM)_{Pn}$ | in-situ mass flux of particle group $P_n$ |
| $(ISM)_p$ | in-situ total mass flux of the Particle Spectrum |
| $M_{TN}$ | mass accumulation (collected mass) in trap N |
| MA | regional measuring site |
| $MP_N$ | measuring location of trap N |
| MV | velocity vector of particles |
| n | particle group index (1, 2, 3, . . . , n) |
| N | trap index (I, II, II, . . . , N) |
| OS | optical sensor |
| P | particle spectrum ($P_1 + P_2 + \ldots + P_n$) |
| $P_1, P_2, \ldots, P_n$ | sinking particle group/gas bubble or other raising particle group |
| $PT_N$ | plate trap N |
| $Q_N$ | fluid flushing rate of trap N |
| QZ | quiescent zone |
| RZ | baffle zone |
| S | substance |
| SM | magazine for sample holders |
| SS | sinking substance |
| $t_N$ | collection time interval of trap N |
| $\tau$ | wall shear stress |
| $\Delta t$ | time interval |
| T | trap (any type and family) |
| TM | trap multiplett |
| TZ | transition zone |
| $u_a$ | approach velocity |
| $u_{dn}$ | deposition velocity |
| VW | sinking/raising velocity spectrum |
| $w_{sn}$ | sinking/raising velocity of particle group $P_n$ |
| $y_n$ | yield function of trap N |

Having thus described the invention what is claimed and desired to be secured by Letters Patent is:

1. A method for systematically determining substances (S) having a particle character which are moving with a vertical component in a fluid flow towards a multiplet of calibrated sediment traps each having known trap and flow parameters, wherein a plurality of accumulation equations are utilized for determining mass accumulations of a plurality of particle groups ($P_1, P_2, \ldots P_n$), the steps of the method comprising:

a) determining trap-specific mass accumulations in a plurality of sediment traps $T_1 \ldots T_N$, wherein the number of the plurality of sediment traps is equal to the number of the plurality of particle groups ($P_1, P_2, \ldots P_n$), each sediment trap having different trap parameters which lie above a range of measuring uncertainties and a sinking/raising velocity spectrum (VM) of the plurality of particle groups ($P_1, P_2, \ldots P_n$); and b) determining a vertical in-situ mass flux $[(ISM)_{Pn}]$ of the plurality of different particle groups ($P_1, P_2, \ldots P_n$) and a derived total in-situ mass flux $[(ISM)_P]$ of a collectable particle spectrum (P) of a free fluid column (FC) representing a regional measuring site (MA) in a multiplicity of selected time intervals ($t_N$) at a plurality of measuring locations ($MP_N$), wherein all of the plurality of particle groups ($P_1, P_2 \ldots P_n$) are present, by solving the plurality of utilized accumulation equations thereby producing concentrations $c_{On}$ of the plurality of particle groups ($P_1, P_2, \ldots P_n$) which, when multiplied by the sinking/raising velocity spectrum (VM), provides the vertical in-situ mass flux $[(ISM)_{Pn}]$ and the derived total in-situ mass flux $[(ISM)_P]$ values.

2. The method according to claim 1, wherein an onset for beginning the multiplicity of selected time intervals ($t_N$) for each of the multiplet of calibrated sediment traps is identical and each has the same duration.

3. The method according to claim 2, wherein the sinking/raising velocity spectrum (VW) of the plurality of particle groups ($P_1, P_2, \ldots P_n$) is determined optically.

4. The method according to claim 3, wherein the plurality of particle groups ($P_1, P_2, \ldots P_n$) are chosen from the group consisting of sinking substances (SS) and substances having variable raising solids-gas combinations in the fluid flow (F).

5. The method according to claim 2, wherein the plurality of particle groups ($P_1, P_2, \ldots P_n$) are chosen from the group consisting of sinking substances (SS) and substances having variable raising solids-gas combinations in the fluid flow (F).

6. The method according to claim 1, wherein the sinking/raising velocity spectrum (VW) of the plurality of particle groups ($P_1, P_2 \ldots P_n$) is determined optically.

7. The method according to claim 6 wherein the plurality of particle groups ($P_1, P_2, \ldots P_n$) are chosen from the group consisting of sinking substances (SS) and substances having variable raising solids-gas combinations in the fluid flow (F).

8. The method according to claim 1, wherein the plurality of particle groups ($P_1, P_2, \ldots P_n$) are chosen from the group consisting of sinking substances (SS) and substances having variable raising solids-gas combinations in the fluid flow (F).

9. An apparatus for systematically determining substances (S, SS) having a particle character which are moving with a vertical component in a fluid flow in a free fluid column (FC) towards a multiplet of calibrated sediment traps ($T_N$, $CT_N$, $PT_N$), each having known trap and flow parameters, wherein a plurality of accumulation equations are utilized for determining mass accumulations of a plurality of particle groups ($P_1, P_2, \ldots P_n$), the apparatus comprising:

a) at least one of the multiplet of calibrated sediment traps ($T_N$, $CT_N$, $PT_N$) of a trap family assigned to a collection cup and a current meter;

b) a trap multiplet (TM) used to determine a vertical in-situ mass flux [$(ISM)_{Pn}$] of the plurality of particle groups ($P_1, P_2, \ldots P_n$) and a derived total in-situ mass flux [$(ISM)_P$] of a particle spectrum (P) of the substances (S, SS) to be determined in the free fluid column (FC) representing a regional measuring site (MA);

c) a number of the plurality of particle groups ($P_1, P_2, \ldots P_n$) is less than or equal to a number of the multiplet of calibrated sediment traps ($T_N$, $CT_N$, $PT_N$); and d) each of the multiplet of calibrated sediment traps ($T_N$, $CT_N$, $PT_N$) having type-specific trap parameters and assigned collection cups (CB) with openings oriented against a sinking/raising movement direction of the plurality of particle groups ($P_1, P_2, \ldots P_n$).

10. The apparatus according to claim 9, wherein each of the multiplet of calibrated sediment traps ($T_N$, $CT_N$, $PT_N$) is assigned to different trap families.

11. The apparatus according to claim 10, wherein at least one of the multiplet of calibrated sediment traps ($T_N$, $CT_N$, $PT_N$) has a hollow geometry with a quiescent zone (QZ) disposed above the collection cup (CB).

12. The apparatus according to claim 11, wherein the trap multiplet comprises a revolving sampling cup magazine (SM) and a multitude of collection cups selectively assigned to one each of the multiplet of calibrated sediment traps ($T_N$, $CT_N$, $PT_N$).

13. The apparatus according to claim 10, wherein an optical sensor is attached within a quiescent zone (QZ) of one of the multiplet of calibrated sediment traps ($T_N$, $CT_N$, $PT_N$) having a hollow geometry, the optical sensor determining a sinking/raising velocity spectrum (VM) of the plurality of particle groups ($P_1, P_2 \ldots P_n$).

14. The apparatus according to claim 13, wherein the trap multiplet comprises a revolving sampling cup magazine (SM) and a multitude of collection cups selectively assigned to one each of the multiplet of calibrated sediment traps ($T_N$, $CT_N$, $PT_N$).

15. The apparatus according to claim 10, wherein the trap multiplet comprises a revolving sampling cup magazine (SM) and a multitude of collection cups selectively assigned to one each of the multiplet of calibrated sediment traps ($T_N$, $CT_N$, $PT_N$).

16. The apparatus according to claim 9, wherein at least one of the multiplet of calibrated sediment traps ($T_N$, $CT_N$, $PT_N$) has a hollow geometry with a quiescent zone (QZ) disposed above the collection cup (CB).

17. The apparatus according to claim 9, wherein an optical sensor is attached within a quiescent zone (QZ) of one of the multiplet of calibrated sediment traps ($T_N$, $CT_N$, $PT_N$) having a hollow geometry, the optical sensor determining a sinking/raising velocity spectrum (VM) of the plurality of particle groups ($P_1, P_2, \ldots P_n$).

18. The apparatus according to claim 17, wherein the trap multiplet comprises a revolving sampling cup magazine (SM) and a multitude of collection cups selectively assigned to one each of the multiplet of calibrated sediment traps ($T_N$, $CT_N$, $PT_N$).

19. The apparatus according to claim 9, wherein an optical sensor is attached within the quiescent zone (QZ) of the hollow geometry trap, the optical sensor determining a sinking/raising velocity spectrum (VM) of the plurality of particle groups ($P_1, P_2, \ldots P_n$).

20. The apparatus according to claim 19, wherein the trap multiplet comprises a revolving sampling cup magazine (SM) and a multitude of collection cups selectively assigned to one each of the multiplet of calibrated sediment traps ($T_N$, $CT_N$, $PT_N$).

21. The apparatus according to claim 9, wherein the trap multiplet comprises a revolving sampling cup magazine (SM) and a multitude of collection cups selectively assigned to one each of the multiplet of calibrated sediment traps ($T_N$, $CT_N$, $PT_N$).

22. The apparatus according to claim 9, wherein the trap multiplet comprises a revolving sampling cup magazine (SM) and a multitude of collection cups selectively assigned to one each of the multiplet of calibrated sediment traps ($T_N$, $CT_N$, $PT_N$).

23. The apparatus according to any one of the preceding claims 9–20, wherein the collection cups (CB) are opened and closed by a timing circuit in response to pre-determined recognized events.

* * * * *